United States Patent [19]
Jinkins

[11] 4,319,136
[45] Mar. 9, 1982

[54] COMPUTERIZED TOMOGRAPHY RADIOGRAPH DATA TRANSFER CAP

[76] Inventor: J. Randolph Jinkins, 1430 North Ave., NE., Atlanta, Ga. 30307

[21] Appl. No.: 92,966

[22] Filed: Nov. 9, 1979

[51] Int. Cl.³ ............................................. G01N 21/00
[52] U.S. Cl. ................................. 250/456; 250/445 T; 250/451; 250/476
[58] Field of Search .................... 250/476, 445 T, 451, 250/456; 128/653, 659

[56] References Cited

U.S. PATENT DOCUMENTS

| | | | |
|---|---|---|---|
| 3,025,397 | 3/1962 | Travis et al. | 250/476 X |
| 3,307,262 | 3/1967 | Chaiken | 250/476 X |
| 3,547,121 | 12/1970 | Cherry | 250/476 X |
| 3,836,776 | 9/1974 | Gullekson | 250/476 X |
| 3,867,634 | 2/1975 | Hounsfield | 250/451 X |
| 3,952,194 | 4/1976 | Bayonnet | 250/476 X |
| 3,974,388 | 8/1976 | Distler et al. | 250/456 X |
| 4,053,781 | 10/1977 | Hounsfield | 250/456 |

Primary Examiner—Davis L. Willis
Attorney, Agent, or Firm—Jones, Thomas & Askew

[57] ABSTRACT

The data transfer for cranial computerized tomography images is substantially form-fitting and dome-shaped. First and second groups of elongated depth markers are positioned in front and in back, diametrically across from each other, and each depth marker extends from the peripheral edge of the cap toward the apex of the cap, the markers are positioned parallel to one another and each marker is graduated in length and terminates at its upper end in an enlargement. A plurality of longitudinal or circumferential markers are positioned between the first and second groups of depth markers and also extend from the peripheral edge of the cap toward the apex of the cap.

8 Claims, 5 Drawing Figures

U.S. Patent  Mar. 9, 1982  Sheet 1 of 2  4,319,136
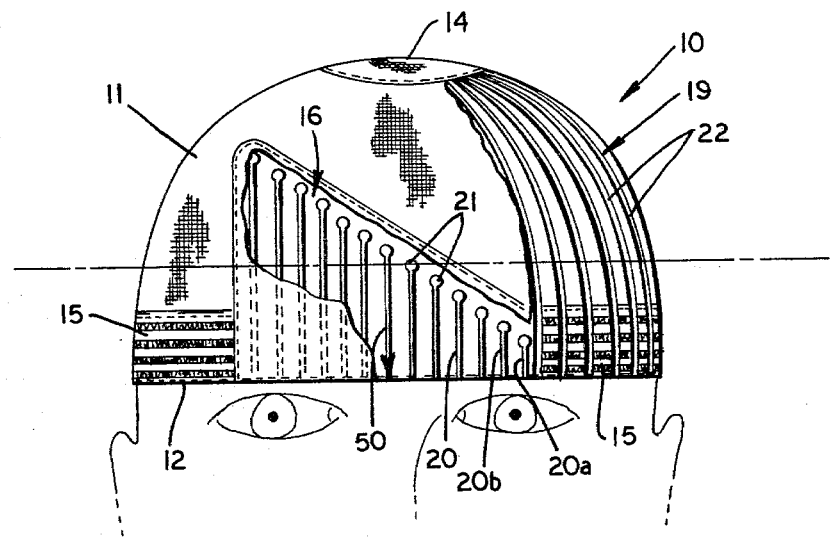
*Fig_1*
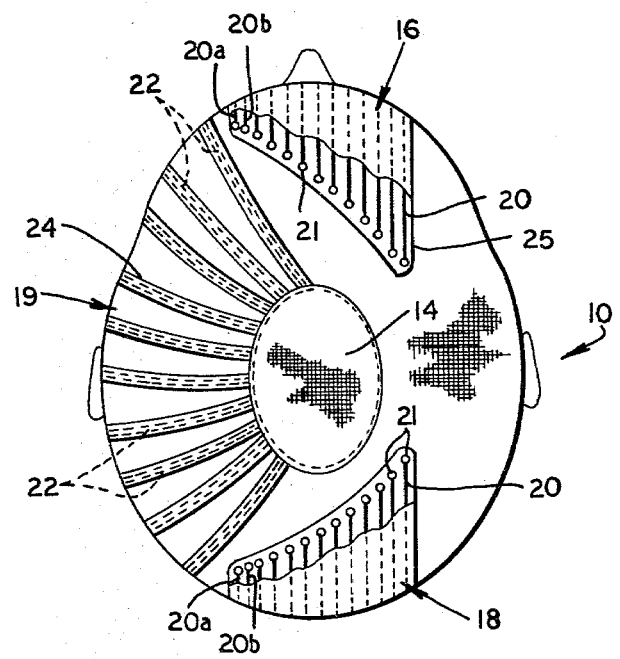
*Fig_2*

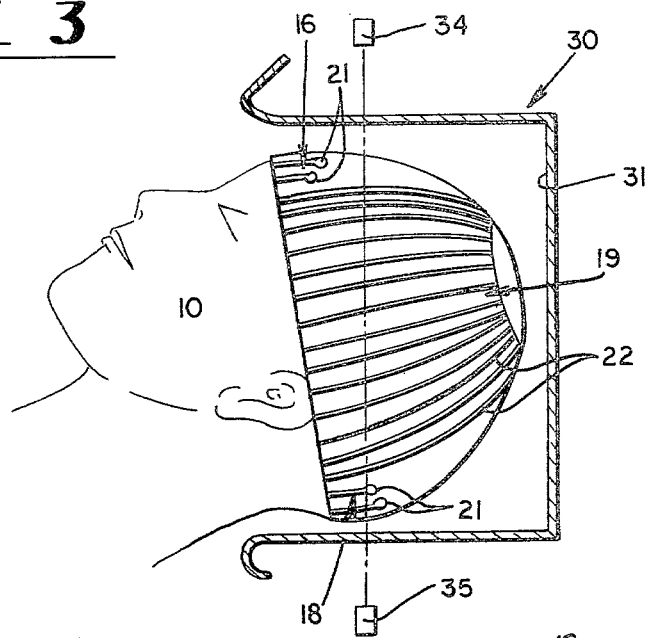
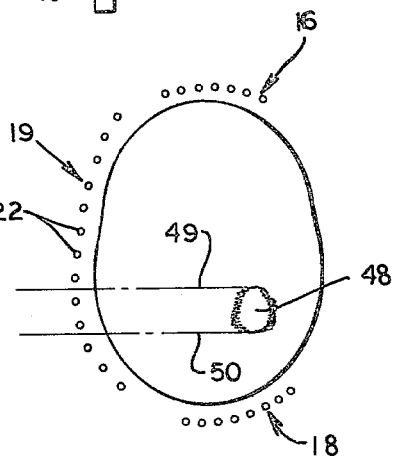
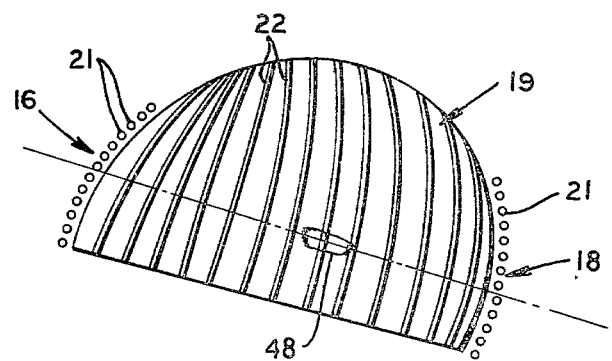

COMPUTERIZED TOMOGRAPHY RADIOGRAPH DATA TRANSFER CAP

BACKGROUND OF THE INVENTION

This invention relates to apparatus for examining the human cranium by means of radiation such as X or γ radiation, and more particularly to a data transfer cap for the cranium which superimposes in the x-ray print a grid which assists the physician in determining the location of a brain lesion, etc.

Computerized tomography scanning devices have been developed for use in producing tomographic x-ray images, particularly images of the skull, as a laminagraphic object. The human head is inserted in a recess of the equipment and radiation is directed through the head from an external source, usually in the form of a set of pencil beams or rays toward detector means disposed on the opposite side of the head. Each ray is detected after it has passed through the body and absorption of radiation by contents of the body disposed along the path in the body followed by each ray is determined. Both the source and the detector means are orbited about the head so that radiation is directed in sets of rays through a plane of the head from a plurality of different directions. In this way the absorption or transmission coefficients of the elements in a two-dimensional matrix of elements can be determined and the result is a plurality of radio graphs that illustrate a plurality of x-ray "slices" or planes through the head.

While the prior art equipment has been very successful in detecting the presence and sizes of lesions and other features of the brain and skull, the precise location of the lesions, etc. is more difficult to determine. It is very difficult to insert a patient's head in the equipment at the precise angle desired, and therefore the data obtained is substantially unreliable. The infinite variety of possible angulations of the computerized tomography image slices about the "ideal" angle of 25° to the infraorbito-meatal line of the human head causes the readout to be unreliable. Due to patient disability or incooperation and simple inadvertent malpositioning, the ideal angle of 25° is often not obtained. This has the effect of placing the sagittal site of a demonstrated lesion in an arc of angles, any of which are theoretical possibilities for the position of the detected lesion, depending on the exact patient position at the time the scan was performed. Even though the scan indication may be of excellent quality, the angulation from the infraorbito-meatal as judged from the CT image is only a very rough estimate of the actual location of the lesion. The lesion can lie at any specific scan angulation within realistic limits, at any point along a vertical arc.

Because of this problem in transfer of location of detected CT abnormalities to the patient, smaller lesions and lesions located over the cerebral convexities can prove to be exceedingly difficult to find in the operating suite, which is likely to cause unnecessary surgical trauma and prolonging of the operative period.

SUMMARY OF THE INVENTION

In an effort to overcome this shortcoming on the part of the cranial CT imaging, a localizing instrument has been devised to transfer the information from the scan, regardless of cranial angulation to the skull radiograph, it being a somewhat more gross representation of the patient being studied.

The basic localizing instrument is a stocking-type elastic cap to which have been permanently applied three sets of commercially available lead salt impregnated 4.1 French polyethylene angiography catheters. The "primary markers" are first and second pluralities of polyethylene tubes of differing lengths graduated in increasing increments of 1.25 centimeters, placed side-by-side and separated by a distance of 0.5 centimeters. One of the identical primary marker sets is applied in a vertical orientation to the anterior portion of the cap and the other primary marker set is applied in vertical orientation to the posterior portion of the cap. When applied, the longest tube of each set should extend superiorly from the lower rim of the cap, corresponding to the supraorbital rim anteriorly and to the base of the occiput posteriorly, to the near its vertex. The disclosed embodiment employs a total of thirteen tubes per primary marker set with a maximum length of 17 centimeters. The superior tips of each tube in the primary marker sets have been heat-flared so that these tips can be identified on the lateral skull radiograph and may be used for subsequent measurement determinations.

The "secondary markers" or circumferential markers are a third set of vertically oriented tubes measuring the height of the stocking cap and applied separately approximately 2.0 centimeters apart along one side of the cap at the lower perimeter thereof, beginning at the lateral edge of the anterior primary marker and continuing posteriorly to the edge of the posterior primary marker. The number of tubes used in the secondary set of the disclosed embodiment is ten. The tubes extend in a vertical direction from the lower perimeter of the cap to converge near its vertex.

The cap is reinforced with strips of elastic bands over the outer surface so that the cap when worn still adhere closely to the scalp. Adhesive tape also may be applied sparingly about the edge of the cap to insure its immobility throughout the examination.

When the scnan procedure has been completed, the accumulated image will have superimposed thereon a grid which indicates the depth and circumferential location of the lesion, etc.

Thus, it is an object of this invention to provide a data transfer cap for cranial computerized tomography images which superimposes a network of elongated depth and circumferential markers on the x-ray or other radiation images which indicate the depth and circumferential location of any lesions, etc, in the human skull.

Another object of this invention is to provide a more reliable means for accurately locating lesions and other objects in a cranial computerized tomography image.

Other objects, features and advantages of the present invention will become apparent upon reading the following specification, when taken in conjunction with the accompanying drawings.

BRIEF DESCRIPTION OF THE DRAWINGS

FIG. 1 is a front view of the data transfer cap, indicating the manner in which the cap fits the patient. The covering over the depth and circumferential markers has been partially removed for clarity.

FIG. 2 is a top view of the data transfer cap of FIG. 1.

FIG. 3 is a schematic side cross sectional view of the apparatus utilized to make the cranial computerized tomography images, showing a patient having the data transfer cap inserted thereon and with the patient's head in the equipment.

FIG. 4 is a data image provided by the equipment illustrated in FIG. 3, showing a computerized tomography image with the information from the data transfer cap superimposed thereon.

FIG. 5 is a conventional X-ray image ed by showing a lateral radiograph with the images from the data transfer cap superimposed thereon.

DETAILED DESCRIPTION

Referring now in more detail to the drawings, in which like numerals indicate like parts throughout the several views, FIG. 1 illustrates a data transfer cap 10 for cranial computerized tomography images which includes a substantially dome-shaped, form-fitting cap structure. The cap structure is formed from a layer of woven or knitted material 11 which is shaped to conform substantially with the upper hemisphere of the human head. The cap structure includes a lower peripheral portion 12 and an upper apex 14, and one or more strips of elastic material 15 are sewn about the cap. At least one strip 15 of elastic material is located adjacent the peripheral portion 12 and the entire structure is substantially stretchable so as to conform with the contour of the head about which the cap is inserted.

As illustrated in FIG. 2, three sets of elongated markers are confined in the cap structure. The first and second plurality of markers 16 and 18 are located diametrically across the cap structure from each other in anterior and posterior positions, and the third set of markers 19 are positioned between the first and second sets.

The first and second sets of markers 16 and 18 are the primary markers and are substantially identical to each other, and each of the first and second sets of markers includes a plurality of elongated depth markers 20 extending from the peripheral edge 12 upwardly toward the apex 14. The markers 20 of the disclosed embodiment are commercially available lead salt impregnated 4.1 French polyethylene angiography catheters. These polyethylene tubes are progressively graduated in length, increasing by increments of 1.25 centimeters from one to the next, with the tubes being placed in side-by-side, parallel relationship and separated by a distance of 0.5 centimeters. For example, tube 20a is the smallest of a series, and the next adjacent tube, tube 20b, is 1.25 centimeters longer than tube 20a. In the disclosed embodiment there are thirteen depth marker tubes 20 for both the anterior set 16 and posterior set 18. Each marker tube 20 terminates at it upper end in an enlarged portion 21. The enlargements or superior tips 21 of each tube in the primary marker sets have been heat-flared so as to be easily identifiable in the resulting graphic display (FIG. 5).

The third set 19 of markers are the "secondary markers" or circumferetial markers and the markers in this set are vertically oriented tubes measuring the approximate height of the data transfer cap and are applied separately approximately 2.0 centimeters apart along the lower peripheral edge 12 of the cap and extend toward the apex 14. The third set 19 comprises individual lead salt impregnated polyethylene catheters 22, with each tube 22 being individually applied with a strip 24 of material and sewn to the base sheet 11 of the cap. Thus, the elasticity of the base sheet 11 as well as the elasticity of the adhesive band 15 permits the tubes 22 of the third set of markers to be movable toward and away from each other as the cap is stretched about the head of the patient. By contrast, the tubes 20 of the first and second plurality of markers are located in the cap structure by means of an overlying, substantially unstretchable sheet 25 sewn over the entire plurality of tubes, with the stitching locating each tube in its proper orientation within the sheet. With this arrangement, the tubes 20 in the anterior and posterior sets 16 and 18 remain in a substantially fixed relationship with respect to one another while the tubes 22 in the circumferential set 19 can be spread apart upon stretching the cap.

When the cap is to be used, it is placed firmly on the head of the patient. If necessary, strips of adhesive tape can be utilized to secure the cap to the patient's head. The patient's head and cap are then inserted into the equipment 30.

As disclosed in U.S. Pat. Nos. 3,867,634, 3,974,388 and 4,053,781, the radiation equipment is operated, causing X or rays to be emitted from the emitter 34 and received by detector 35, and the absorption of the radiation by the contents of the head of the patient disclosed along a path in the body followed by each ray is determined. The source 34 and detector means 35 are orbited relative to the head of the patient so that radiation is directed, in sets of rays, through a plane of the head from a plurality of different directions. In this way the absorption or transmission coefficients of the elements in a two-dimensional matrix of elements notionally disposed in the plane of the head can be determined, provided sufficient rays are directed through the body.

As illustrated in FIG. 4, where a CT image is displayed, a theoretical lesion 48 is indicated. In order to detect the depth of the lesion 48 within the head, the primary sets of markers 16 and 18 are used. It will be noted from FIG. 4 that in the anterior set 16 of primary markers, seven markers are detected, while in the posterior set 18 there are eight markers detected. When referring to FIG. 5, the depth of the lesion 48 can be determined by counting downwardly the enlarged protrusions 21 of the depth markers on the lateral skull radiograph in both the anterior and posterior positions. In the example disclosed, the depth of the lesion 48 would be determined by counting down seven of the enlargements 21 in the anterior set and down by eight of the enlargements 21 in the posterior set, and then extending a line from the seventh and eighth enlargements across the lateral skull radiograph. Thus, the markers 20 and their enlargements 21 function as depth markers.

In order to get the circumferential location of the lesion 48, construction lines 49 and 50 are extended laterally from the lesion indication 48 on the CT image (FIG. 4) until the construction lines 49 and 50 intersect the arc of the circumferential markers 22. The circumferential markers 22 can then be counted on the lateral skull radiograph to locate the lesion 48 in the position indicated at FIG. 5.

Larger lesions can be further delineated using the previously-described method. If the lesion is of sufficient size to overlap into an adjoining section made by the CT apparatus, the lesion can be plotted on the lateral radiograph in the same manner and a grid or map of the lesion can be obtained.

On the exterior surface of the cap (FIG. 1) a mark 50 is formed so as to indicate to the operator how the cap is to be oriented on the patient's head. The mark 50 is to be aligned with the center of the nose of the patient. The cap is sized and shaped to fit the average sized patient's head.

While the markers 20 and 22 have been described as commercially available lead salt impregnated French polyethylene angiographic catheters, it will be understood that any similar type somewhat flexible elongated strip of material either made with or impregnated with a substance that can be read in a radiograph is usable. It is not necessary that the markers be tubular in cross section.

Moreover, the data transfer cap 10 has been disclosed with anterior and posterior primary sets of markers and with a single side set of markers. If a radiograph is to be taken from the other side of the patient's head, the transfer cap can be everted in order to position the side markers on the other side of the patient's head.

Also, while the primary sets of markers, the anterior and posterior markers, have been indicated as progressively graduated in length, it is not necessary that the graduated lengths be progressive. For example, it is desirable for the anterior and posterior markers 16 and 18 to be graduated in length, but the arrangement could have the markers in various staggered relationship, for example the longest marker being in the center of the group.

It should be understood, of course, that the foregoing relates to only a preferred embodiment of the present invention and that numerous modifications or alterations may be made therein without departing from the spirit and scope of the invention as set forth in the appended claims.

I claim:

1. A data transfer cap for cranial computerized tomography images comprising a substantially form-fitting dome-shaped cap including a peripheral edge and an apex, a first plurality of elongated depth markers extending from the peripheral edge toward the apex of said cap, a second plurality of elongated depth markers located diametrically across from the first plurality and also extending from the peripheral edge toward the apex of the cap, said depth markers of each plurality of depth markers being graduated in height and extending a different distance from the other markers from the peripheral edge toward the apex of the cap, and a plurality of circumferential markers located between the first and second plurality of depth markers extending from the peripheral edge toward the apex of the cap.

2. The data transfer cap of claim 1 and wherein the depth markers of each of said first and second plurality of depth markers are retained by a substantially non-stretchable sheet of material in parallel relationship with respect to one another when the cap is placed on a patient's head.

3. The data transfer cap of claim 1 and wherein the superior end portion of each depth marker adjacent the apex of the cap is larger than the rest of the depth marker.

4. The data transfer cap of claim 1 and wherein the depth markers of each plurality of depth markers are equally spaced along the peripheral edge of the cap and are progressively graduated in length by approximately 1.25 centimeters and are spaced apart from one another a distance of approximately 0.5 centimeters, and wherein the longitudinal markers are spaced apart from one another at the peripheral edge of the cap a distance of approximately 2.0 centimeters.

5. The data transfer cap of claim 1 and further including an elastic band forming a part of said cap for causing the cap to snugly fit the head of the patient.

6. A data transfer cap for cranial computerized tomography images comprising a substantially form-fitting dome-shaped cap including a peripheral portion and an apex, a plurality of elongated depth and circumferential markers spaced about the peripheral portion of said cap and extending from the peripheral portion toward the apex of said cap, said depth markers extending different distances from the peripheral portion toward the apex of said cap to indicate in a computerized tomography image the depth and plane at which an image is taken through the cranium.

7. The data transfer cap of claim 6 and wherein said elongated depth markers comprises first and second groups of markers positioned diametrically across the cap from each other and the markers in each group extending approximately parallel to one another and the markers each including an enlarged end portion adjacent the apex.

8. A data transfer cap for cranial computerized tomography images comprising a substantially form-fitting dome-shaped cap, a grid of elongated markers of progressive graduated size extending in a pattern throughout said cap, said markers being detectable on a radiograph of the cap and the head upon which the cap is positioned so as to provide location reference marks on said radiograph.

* * * * *